United States Patent
Bailly et al.

(10) Patent No.: US 7,816,342 B2
(45) Date of Patent: Oct. 19, 2010

(54) ANTI-OBESITY COMPOSITIONS

(75) Inventors: Jacques Bailly, Rixheim (FR); Rainer Eugen Martin, Grenzach-Wyhlen (AT); Susanne Raab, Leinfelden-Echterdingen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/348,828

(22) Filed: Feb. 7, 2006

(65) Prior Publication Data

US 2006/0135471 A1   Jun. 22, 2006

Related U.S. Application Data

(63) Continuation of application No. 10/421,111, filed on Apr. 23, 2003, now abandoned.

(30) Foreign Application Priority Data

Apr. 26, 2002   (EP) .................................. 02009254

(51) Int. Cl.
*A61K 31/715* (2006.01)
*A61K 31/335* (2006.01)
*A01N 43/02* (2006.01)

(52) U.S. Cl. ........................................ 514/54; 514/449

(58) Field of Classification Search ................. 514/449, 514/290; 424/401, 439, 441, 464, 738; 510/418; 549/328
See application file for complete search history.

(56) References Cited

U.S. PATENT DOCUMENTS

| | | | | |
|---|---|---|---|---|
| 4,582,714 A | * | 4/1986 | Ford et al. | .................. 426/564 |
| 4,598,089 A | * | 7/1986 | Hadvary et al. | ............. 514/449 |
| 5,447,953 A | | 9/1995 | Isler et al. | |
| 5,486,364 A | * | 1/1996 | King et al. | .................. 424/488 |
| 5,942,500 A | * | 8/1999 | Perry | .......................... 514/55 |
| 6,004,996 A | | 12/1999 | Shah et al. | |
| 6,093,439 A | | 7/2000 | Whaley et al. | |
| 6,358,522 B1 | | 3/2002 | Hug et al. | |
| 6,534,087 B2 | * | 3/2003 | Busson et al. | ................ 424/464 |
| 6,558,690 B2 | * | 5/2003 | Portman | ..................... 424/439 |
| 2002/0035089 A1 | | 3/2002 | Barbier et al. | |

FOREIGN PATENT DOCUMENTS

| | | |
|---|---|---|
| WO | WO 00/09122 | 2/2000 |
| WO | WO 00/09123 | 2/2000 |
| WO | WO 02/00201 | 1/2002 |

OTHER PUBLICATIONS

Cavaliere et al. International Journal of Obesity (2001) 25, 1095-1099.*
Arvill et al. Am J Clin Nutr 1995; 71:585-9.*
Ebihara et al. The Journal of Nutrition (1989), 119(8), 1100-6.*

* cited by examiner

*Primary Examiner*—Shaojia Anna Jiang
*Assistant Examiner*—Layla Bland
(74) *Attorney, Agent, or Firm*—George W. Johnston; Dennis P. Tramaloni; Brian C. Remy

(57) ABSTRACT

The present invention relates to compositions and methods for treating obesity. More particularly, the invention relates to a composition comprising a lipase inhibitor such as orlistat, and glucomannan such as konjac as well as methods for utilizing such compositions and kits for carrying out this method.

42 Claims, 2 Drawing Sheets

Figure 1:
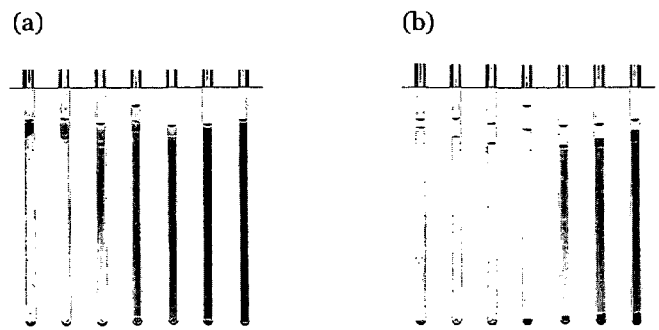

Both $t = 1$ min (a) and $t = 300$ min (b) from left to right: reference (mixture soya oil/buffer); $c = 0.01\%$, $c = 0.1\%$; $c = 0.5\%$; $c = 1.0\%$; $c = 1.5\%$; $c = 2.0\%$ (w/w).

Both $t = 1$ min (a) and $t = 300$ min (b) from left to right: reference (mixture soya oil/buffer) at pH = 7; pH = 4; pH = 5; pH = 6; pH = 7; pH = 8; pH = 9.

ANTI-OBESITY COMPOSITIONS

PRIORITY TO RELATED APPLICATIONS

This application is a continuation of U.S. application Ser. No. 10/421,111, filed Apr. 23, 2003, now abandoned which claims the benefit of European Application No. 02009254.0, filed Apr. 26, 2002. The entire contents of the above-identified applications are hereby incorporated by reference.

FIELD OF THE INVENTION

The field of this invention is the field of combating obesity utilizing compositions containing lipase inhibitors.

BACKGROUND OF THE INVENTION

Adverse effects which occasionally are observed in patients treated with lipase inhibitors are anal leakage of oil (oily spotting) and fecal incontinence. Oily spotting results from physical separation of some of the ingested but unabsorbed dietary fat from the bulk of the fecal mass in the colon.

In U.S. Pat. No. 5,447,953 it has been shown that by combining a lipase inhibitor with substantial amounts of water insoluble crude fibers, the inhibiting effect on fat absorption can be increased. International Patent Application WO 00/09123 demonstrates that by combining a lipase inhibitor such as orlistat with low amounts of chitosan or a derivative or a salt thereof, the phenomenon of anal leakage of oil can be strongly reduced. Various approaches to control oily leakage have been discussed. Among such strategies are i) use of a surfactant to stabilize the oil/water interface in order to prevent coalescence of the oil emulsion in the colon, ii) enhancing water viscosity in the colon to reduce both intensity and frequency of droplet-droplet interactions and by that reducing the probability of coalescence, iii) physical absorption of oil by a lipophilic compound, or iv) increasing the natural stool mass by facilitating bacterial growth in the colon.

SUMMARY OF THE INVENTION

The present invention relates to pharmaceutical compositions and methods for preventing and treating obesity. More particularly, the invention relates to a composition comprising a lipase inhibitor, preferably a compound of formula I (orlistat),

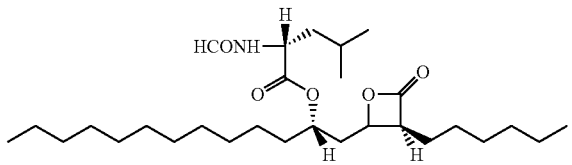

(I)

and glucomannan, optionally containing one or more pharmaceutically acceptable excipients.

The invention also relates to the compositions as described above for use in the treatment and prevention of obesity and to a process for preparing a composition as described above, comprising mixing a lipase inhibitor with glucomannan and optionally one or more pharmaceutically acceptable excipients.

The invention also refers to a kit for treatment of obesity, said kit comprising a) a first component which is a lipase inhibitor and b) a second component which is glucomannan as defined above, e.g. in an oral unit dosage form, preferably comprising a) from 1 to 100 doses units of orlistat and b) from 1 to 100 doses units of a glucomannan.

Another embodiment of the present invention refers to a kit for treatment of obesity, said kit comprising a) a first component which is a lipase inhibitor and b) a second component which is glucomannan in oral unit dosage forms.

The present invention also relates to the use of a composition as defined above in the manufacture of medicaments useful for the treatment and prevention of obesity and to the use of a lipase inhibitor as defined above in the manufacture of a medicament for the treatment and prevention of obesity in a patient who is also receiving treatment with glucomannan as defined above. This use of glucomannan and lipase inhibitor refers to the simultaneous, separate or sequential use for the treatment and prevention of obesity.

Further the invention is directed to a method of treatment of obesity in a human in need of such treatment which comprises administration to the human of a therapeutically effective amount of a lipase inhibitor and a therapeutically effective amount of glucomannan as defined above. The method refers to the simultaneous, separate or sequential administration of the compounds. A further embodiment of the present invention is a lipase inhibitor and glucomannan or konjac as defined above as a combined preparation for simultaneous, separate or sequential use for the treatment and prevention of obesity. The invention also refers to the use of glucomannan or konjac as defined above in the manufacture of medicaments useful for the treatment and prevention of gastrointestinal side effects selected from the group of oily spotting, fatty/oily stools, fecal urgency, increased defecation and fecal incontinence and to a method of treatment or prevention of gastro-intestinal side effects selected from the group of oily spotting, fatty/oily stools, fecal urgency, increased defecation and fecal incontinence in a human in need of such treatment which comprises administration to the human of a therapeutically effective amount of konjac or glucomannan as defined above. Further the invention is directed to a lipase inhibitor and glucomannan or konjac as defined above for simultaneous, separate or sequential use for the treatment and prevention of obesity.

FIGURES

FIG. 1 displays test emulsions of konjac after centrifugation at 3100 g for t=1 min (a) and t=300 min (b), respectively. After a centrifugation time of t=300 min, only for emulsions containing konjac in concentrations higher than 1.5% (w/w) a weak emulsification stabilization is observed.

Figure 2:
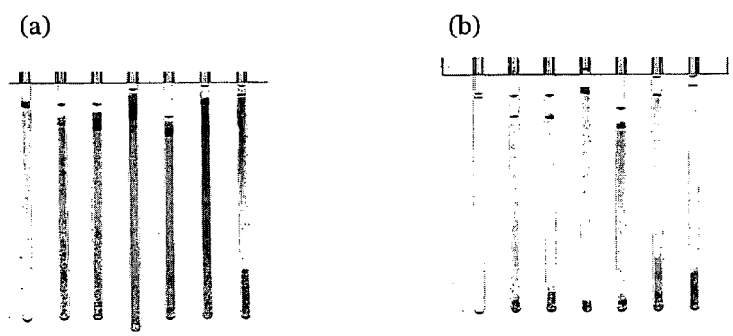

FIG. 2 shows test emulsions of konjac after centrifugation at 3100 g for t=1 min (a) and t=300 min (b), respectively. The emulsions contained 1.0% (w/w) konjac at different pH values. After a centrifugation time of t=300 min minor emulsion stabilization was observed at pH 6 and 7, respectively. For all other emulsions extensive coalescence was observed.

Figure 3:
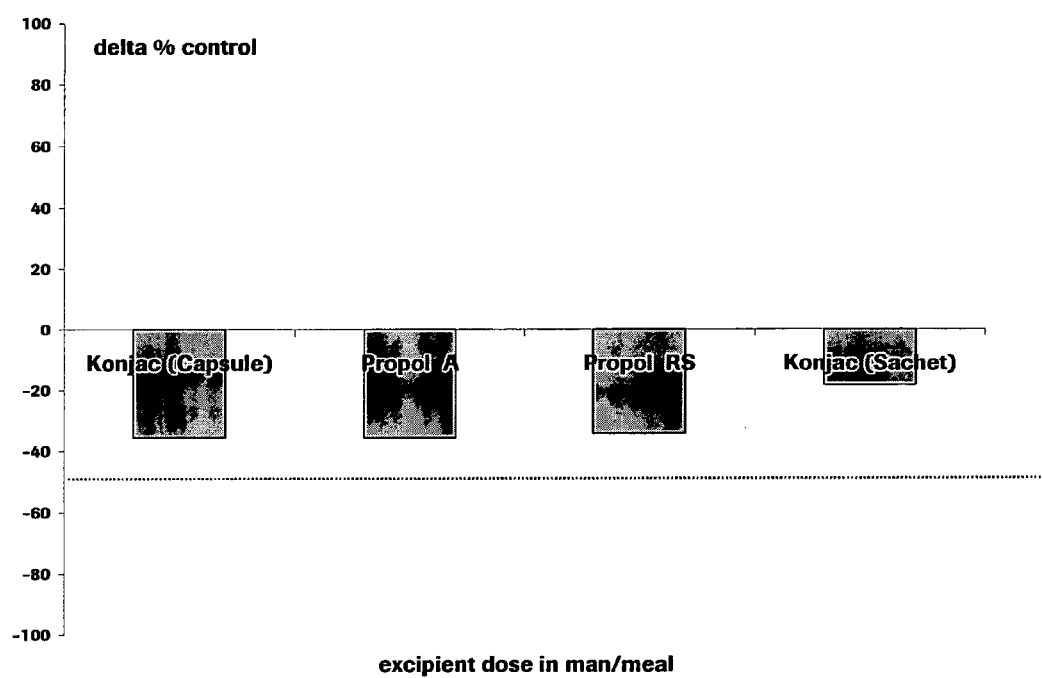

FIG. 3: The free oil reducing effect of different types of glucomannan in % relative to controls (data as means±SE).

DETAILED DESCRIPTION OF THE INVENTION

In accordance with this invention the administration of glucomannan in conjunction with lipase inhibitors for combating obesity reduces the gastro-intestinal side effects produced by the lipase inhibitor such as oily spotting, fatty/oily stools, fecal urgency, increased defecation and fecal incontinence in humans.

In accordance with an embodiment of this invention, pharmaceutical compositions are provided which contain the lipase inhibitors, preferably orlistat, and glucomannan. These compositions may contain pharmaceutically acceptable excipients. In accordance with one embodiment, the pharmaceutical composition contains from about 0.1% by weight to about 10% by weight, based upon the weight of the composition, of the lipase inhibitor and from about 10% by weight to about 75% by weight, based upon the weight of the composition, of glucomannan and from about 0.1% to 90% by weight, based upon the weight of the composition of one or more pharmaceutically acceptable excipients. Generally it is preferred that the composition of this invention be formulated in a unit oral dosage form.

In accordance with another embodiment of this invention there is provided a method for combating obesity in human patients by administering to said human patients the lipase inhibitor, preferably orlistat, in an effective amount to treat said obesity, in conjunction with glucomannan. In accordance with a preferred embodiment both the glucomannan and lipase inhibitor can be orally administered in conventional oral dosage forms such as through the compositions of this invention. In accordance with this invention, the glucomannan and lipase inhibitor can be administered simultaneously, separately or sequentially for carrying out the method of this invention. Generally, it is preferred, when separately administered, the two components i.e. the lipase inhibitor and the glucomannan be administered within two hours of each other. In accordance with this invention the glucomannan which is administered in conjunction with lipase inhibitor is administered in an amount of about 0.5 g to 10 g per day after administration of lipase inhibitor. In accordance with this invention the lipase inhibitor is generally administered from 2 to preferably 3 times per day.

In accordance with another embodiment of this invention there is provided a kit containing the lipase inhibitor, preferably orlistat as one component, and the glucomannan as the second component. Preferably, each of the components contains the glucomannan and lipase inhibitor, such as orlistat, in the compositions in oral unit dosage forms. The first or lipase inhibitor component of the kit can contain from 1 to 100 oral dosage units of the lipase inhibitor, such as orlistat, and the second or glucomannan component contains from about 1 to 100 oral dosage units of glucomannan. Lipase inhibitor is present in each oral unit dosage form in an amount of from 5 to 120 mg and the glucomannan is provided in a separate oral unit dosage form which constitutes the second component. In accordance with a preferred embodiment of this invention, the glucomannan can be provided in the separate oral unit dosage form in an amount of from about 0.5 g to about 10 g. Generally it is preferred that the orlistat be administered in an amount of from 16 mg to 720 mg in each unit oral dosage form contained within the first component of the kit.

In accordance with this invention, it has been found that glucomannan can be administered such as glucomannan itself or in the form of konjac, e.g. konjac flour, in any amount sufficient to reduce the gastro-intestinal adverse events (GI-AE) commonly observed after administration of a lipase inhibitor such as orlistat or artificial fat substitutes. Therefore the method of this invention involves the use of glucomannan in an amount sufficient to reduce the gastro-intestinal adverse effects observed after administration of a lipase inhibitor. These effects include oily spotting, fatty/oily stools, fecal urgency, increased defecation and fecal incontinence in humans.

Konjac (*Amorphophallus konjac*) is a plant, the tuber of which is the source of a well-known foodstuff in China and Japan, namely konjac flour. This flour comprises a highly viscous sol of glucomannan and soluble starches when reconstituted in water. The principal soluble constituent is glucomannan (formula II), a polysaccharide comprised of D-glucose and D-mannose, which is useful as an ingredient in various foodstuffs, as well as in industrial applications such as films, oil drilling fluids and paints.

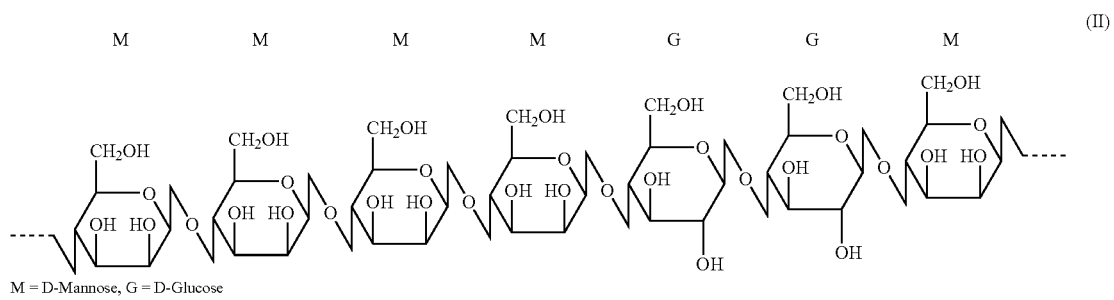

In accordance with this invention any effective amount of lipase inhibitors for combating obesity can be administered to human patients. The use of these lipase inhibitors and their dosages are well known for combating obesity. By combating obesity, it is meant that the composition of this invention can be utilized either for prevention and/or treatment of obesity. In addition the compositions of this invention can contain any effective amount of the lipase inhibitor needed for administration to combat obesity.

Where the glucomannan is to be separately or simultaneously administered, in accordance with another embodiment of this invention, kits can be provided containing the Accordingly, the present invention refers to a composition comprising a lipase inhibitor and glucomannan. Unless otherwise indicated the following definitions are set forth to illustrate and define the meaning and scope of the various terms used to describe the invention herein.

The term "lipase inhibitor" refers to compounds which are capable of inhibiting the action of lipases, for example gastric and pancreatic lipases. For example, orlistat and lipstatin as described in U.S. Pat. No. 4,598,089 are potent inhibitors of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, *J. Antibiot.*, 47(12):1369-1375 (1994)). The term "lipase inhibitor" refers also to polymer bound lipase inhibitors for example described in International Patent Application WO 99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" also refers to 2-oxy-4H-3,1-benzoxazin-4-ones which have been described in International Patent Application WO 00/40569 (Alizyme Therapeutics Ltd.), e.g. 2-decyloxy-6-methyl-4H-3,1-benzoxazin-4-one, 6-methyl-2-tetradecyloxy-4H-3,1-benzoxazin-4-one, and 2-hexadecyloxy-6-methyl-4H-3,1-benzoxazin-4-one and other oxetanones described for example in International Patent Applications WO 01/32616, WO 01/32669 and WO 01/32670. Most preferably, the term "lipase inhibitor" refers to orlistat.

Orlistat is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 185,359, 189,577, 443,449, and 524,495.

Orlistat is preferably orally administered from 60 to 720 mg per day in divided doses two to three times per day. Preferred is wherein from 180 to 360 mg, most preferably 360 mg per day of a lipase inhibitor is administered to a human subject, preferably in divided doses two or, particularly, three times per day. The subject is preferably an obese or overweight human, i.e. a human with a body mass index of 25 or greater. Generally, it is preferred that the lipase inhibitor be administered within about one or two hours of ingestion of a meal containing fat.

Orlistat can be administered to humans in conventional oral compositions, such as tablets, coated tablets, hard and soft gelatin capsules, emulsions or suspensions. Examples of carriers which can be used for tablets, coated tablets, dragées and hard gelatin capsules are lactose, other sugars and sugar alcohols like sorbitol, mannitol, maltodextrin, or other fillers; surfactants like sodium lauryl sulfate, Brij 96, or Tween 80; disintegrants like sodium starch glycolate, maize starch or derivatives thereof; polymers like povidone and crospovidone; talc; stearic acid or its salts and the like. Suitable carriers for soft gelatin capsules are, for example, vegetable oils, waxes, fats, semi-solid and liquid polyols and the like. Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents and antioxidants. They can also contain still other therapeutically valuable substances. The formulations may conveniently be presented in unit dosage form and may be prepared by any methods known in the pharmaceutical art. Preferably, orlistat is administered according to the formulation shown in the Examples and in U.S. Pat. No. 6,004,996, respectively.

The term "konjac flour" refers to a hydrocolloidal polysaccharide obtained from the tubers of species of *Amorphophallus konjac*. The perennial tuber is unique to Asia and especially cultivated in Japan. Konjac flour is a high molecular weight, nonionic glucomannan consisting primarily of mannose and glucose molecules combined in a mole ratio of 1.6:1.0. It is a slightly branched polysaccharide connected by beta 1-4 linkages and has an average molecular weight ranging from 200,000 to 2,000,000 daltons. Acetyl groups along the glucomannan backbone contribute to its solubility and are located, on average, at every 9 to 19 sugar unit. Refined konjac flour is easily soluble in cold water and forms a highly viscous solution with a pH between 4.0 and 7.0. Addition of a mild alkaline solution results in the formation of a heat-stable gel that resists melting, even under extended heating conditions. The purification process for konjac flour is carried out in large-scale extraction plants. The konjac tubers are first pulverized, and then the collected glucomannan particles are polished in order to dislodge and extract noxious materials adhering to them. This process yields a refined konjac flour with high degree of purity that improves product solubility, stability and overall functionality. The particles are tasteless, odorless and white in color.

Konjac flour and glucomannan (PROPOL®, RHEOLEX®) are commercially available products (Kyoei Konnyaku, Inc., Behr, Wunderlich & Co., Provisco, FMC Biopolymers, Naturland, SiberHegner and Co. Ltd.). The preparation and use have been described e.g. in U.S. Pat. Nos. 3,767,424, 3,973,007, 4,588,589, 5,486,364, 5,486,364, 5,733,593, 5,536,521, 6,126,906, etc.

The term "pharmaceutically acceptable" as used herein means that the corresponding compounds are acceptable from a toxicity viewpoint.

In more detail, the present invention relates to a pharmaceutical composition comprising a lipase inhibitor and glucomannan. Optionally this composition may contain one or more pharmaceutically acceptable excipients. The glucomannan may be provided in form of konjac. Preferably, the konjac contains at least 80% by weight glucomannan, more preferably at least 90% by weight glucomannan. The glucomannan or konjac may be provided in form of konjac powder, e.g. konjac flour. Preferably the lipase inhibitor is orlistat. These 80% by weight are based on the total weight of the composition.

Pharmaceutical compositions incorporating both a compound of a lipase inhibitor and glucomannan are important embodiments of the present invention. Such pharmaceutical compositions comprise a therapeutically effective amount of each of the compounds for the given purpose. Each dosage unit can obtain the daily doses of both compounds or may contain a fraction of the daily dose, such as one-third of the doses. Alternatively, each dosage unit may contain the entire dose of one of the compounds, and a fraction of the dose of the other compound. In such case the patient would daily take one of the combination dosage units, and one or more units containing only the other compound.

In a preferred embodiment of the present invention the composition comprises a) 0.1 to 20% (w/w) lipase inhibitor, b) 10 to 75% (w/w) glucomannan such as konjac, and c) 0.1 to 90% (w/w) of one or more pharmaceutically acceptable excipients. More preferably, a composition may comprise a) 0.1 to 10% (w/w) lipase inhibitor, b) 20 to 75% (w/w) glucomannan and c) 0.1 to 90% (w/w) of one or more pharmaceutically acceptable excipients. Preferably, the amount of one or more pharmaceutically acceptable excipients is from about 5 to 50% (w/w), more preferably 5 to 20%. In more detail, the composition may contain a) from about 5 to about 1000 mg lipase inhibitor, e.g. orlistat, in an amount of e.g. from about 10 to about 500 mg lipase inhibitor, preferably from about 20 to about 100 mg lipase inhibitor, e.g. from about 10 to about 360 mg orlistat, more preferably from about 30 to about 120 mg orlistat, more preferably from about 40 to about 80 mg orlistat and b) from about 0.5 to about 10 g glucomannan, preferably from about 0.5 to about 8 g glucomannan, and more preferably from about 0.5 to about 6 g glucomannan. The weight percent is based upon the total weight of the composition The pharmaceutically acceptable excipients may be selected from the group consisting of fillers, surfactants, disintegrants, binders, lubricants, flowability enhancers, sweeteners, and colorants, e.g. a composition may comprise of a) about 5 to about 1000 mg lipase inhibitor; b) about 0.5 to about 10 g glucomannan; and optionally pharmaceutically acceptable excipients selected from the group of about 0.1 to about 10 g fillers, about 0.05 to about 5.0 g surfactants, about 0.05 to about 2.0 g disintegrants, about 0.02 to about 5.0 g binder, about 0.001 to about 1.0 g lubricants, about 0.1 to about 5.0 g flowability enhancers, about 0.01 to about 4.0 g sweeteners, and about 0.001 to about 0.5 g colorants.

The pharmaceutically acceptable excipients may be selected from the group consisting of fillers, e.g. sugars and/or sugar alcohols, e.g. lactose, sorbitol, mannitol, maltodextrin, etc.; surfactants, e.g. sodium lauryl sulfate, TPGS, Brij 96 or Tween 80; disintegrants, e.g. sodium starch glycolate, maize starch or derivatives thereof; binder, e.g. povidone, crosspovidone, polyvinylalcohols, hydroxypropylmethylcellulose; lubricants, e.g. stearic acid or its salts; flowability enhancers, e.g. silicium dioxide; sweeteners, e.g. aspartame; and/or colorants, e.g. β-carotene.

In a preferred embodiment of the present invention the composition comprises a) about 0.1 to about 20% (w/w) lipase inhibitor; b) 10 to about 75% (w/w) glucomannan such as konjac; and optionally pharmaceutically acceptable excipients selected from the group of about 0.1 to about 20% (w/w) fillers, about 0.1 to about 10% (w/w) surfactants, about 0.1 to about 10% (w/w) disintegrants, about 0.1 to about 10% (w/w) binder, about 0.1 to about 10% (w/w) lubricants, about 0.1 to about 10% (w/w) flowability enhancers, about 0.1 to about 10% (w/w) sweeteners, and about 0.1 to about 5% (w/w) colorants.

In more detail, the composition may contain a) from about 5 to about 1000 mg lipase inhibitor, e.g. orlistat, in an amount of e.g. from about 10 to about 500 mg lipase inhibitor, preferably from about 20 to about 100 mg lipase inhibitor, e.g. from about 10 to about 360 mg orlistat, more preferably from about 30 to about 120 mg orlistat, more preferably from about 40 to about 80 mg orlistat and b) from about 0.5 to about 10 g glucomannan, preferably from about 0.5 to about 8 g glucomannan, and more preferably from about 0.5 to about 6 g glucomannan.

Oral dosage forms are the preferred compositions for use in the present invention and these are the known pharmaceutical forms for such administration, for example tablets, capsules, bars, sachets, granules, syrups and aqueous or oily suspensions. The pharmaceutically acceptable excipients (diluents and carriers) are known in the pharmacist's art. Tablets may be formed from a mixture of the active compounds with fillers, for example calcium phosphate; disintegrating agents, for example maize starch, lubricating agents, for example magnesium stearate; binders, for example microcrystalline cellulose or polyvinylpyrrolidone and other optional ingredients known in the art to permit tabletting the mixture by known methods. Similarly, capsules, for example hard or soft gelatin capsules, containing the active compound with or without added excipients, may be prepared by known methods. The contents of the capsule may be formulated using known methods so as to give sustained release of the active compound. For example, the tablets and capsules may conveniently each contain the amounts of lipase inhibitor and glucomannan as described above.

Other dosage forms for oral administration include, for example, aqueous suspensions containing the active compounds in an aqueous medium in the presence of a non-toxic suspending agent such as sodium carboxymethylcellulose, and oily suspensions containing the active compounds in a suitable vegetable oil, for example arachis oil, olive oil or myritol 318. The active compounds may be formulated into granules with or without additional excipients. The granules may be ingested directly by the patient or they may be added to a suitable liquid carrier (e.g. water) before ingestion. The granules may contain disintegrants, e.g. an effervescent pair formed from an acid and a carbonate or bicarbonate salt to facilitate dispersion in the liquid medium.

In the compositions of the present invention the active compounds may, if desired, be associated with other compatible pharmacologically active ingredients. Optionally vitamin supplements may be administered with the compounds in accordance with the present invention. Both compounds, the lipase inhibitor and glucomannan, may be administered simultaneously, separately or sequentially (e.g. orlistat as described above and glucomannan in the evening). Preferably, the compounds or compositions are administered during a meal or 1-2 hours before or after a meal. The amount of glucomannan to be administered will depend on a number of factors including the age of the patient, the severity of the condition and the past medical history of the patient and lies within the discretion of the administering physician.

The invention will be better understood by reference to the following examples which illustrate but do not limit the invention described herein.

EXAMPLES

Example 1

In Vitro Studies

Surprisingly, it has now been observed that glucomannan is active in reducing gastro-intestinal adverse events (GI-AE) commonly observed after administration of a lipase inhibitor such as orlistat.

The interaction of konjac (source of glucomannan) with oil and water was examined by an absorption test. Samples of the compound were brought into contact with either soya oil or simulated intestinal fluid (SIF, phosphate buffer without pancreatin) and incubated for 24 h at 37° C. Remaining liquid was separated from the solid material by means of centrifugation (3×5 min at 3100 g). Whereas in SIF significant swelling of the polymer was observed, no swelling occurred in soya oil. The SIF and soya oil absorption capacity of konjac was calculated to 4.8 g/g and 0.5 g/g, respectively. The low amount of oil binding demonstrates its poor lipophilicity.

The coalescence behavior of emulsions stabilized with konjac was probed using a centrifugal method. With this in vitro method, both concentration and pH-depended emulsion stabilities were examined. The results of these stability studies are listed in Tables 1 and 2. The use of konjac in less than 0.5% (w/w) revealed very unstable emulsions resulting in rapid oil/water phase separation (Table 1). Even at konjac concentrations of 1.0% (w/w), emulsions remained rather unstable and clear phase separation was obtained after 10 min centrifugation. Only emulsions containing more than 1.0% (w/w) konjac exhibited after centrifugation times of up to t=300 min medium stability with the emulsion partly broken (FIG. 1).

TABLE 1

Stability of konjac test emulsions at various concentrations c and centrifugation times t.

| | Emulsion Stability Konjac t/min | | | | | | | | |
|---|---|---|---|---|---|---|---|---|---|
| c (% w/w) | 1 | 10 | 40 | 70 | 100 | 130 | 160 | 220 | 300 |
| 0.01 | l* | l | l | l | l | l | l | l | l |
| 0.1 | l | l | l | l | l | l | l | l | l |
| 0.5 | l | l | l | l | l | l | l | l | l |
| 1.0 | m | l | l | l | l | l | l | l | l |
| 1.5 | h | m | m | m | m | m | m | m | m |
| 2.0 | h | m | m | m | m | m | m | m | m |

*l = low stability: oil and water form two distinct clearly separated phases;
m = medium stability: emulsion partly broken;
h = high stability: no indications of coalescence, optically non-transparent, stable emulsion FIG. 1 displays test emulsions of konjac after centrifugation at 3100 g for t=1 min (a) and t=300 min (b), respectively. After centrifugation times of t=300 min, only for emulsions containing konjac in concentrations higher than 1.5% (w/w) a weak emulsification stabilization is observed.

In order to investigate emulsion stability at different pH values, test emulsions with a constant konjac concentration of c=1.0% (w/w) covering a pH range of 4 to 9 were prepared (Table 2). At both extreme pH values of 4 and 9 very poor emulsification of the test emulsions was observed, resulting in instantaneous layering of the oil phase. Whereas at pH=8 short centrifugation times of less than 30 min also led to complete emulsion breaking, emulsions at pH=5 revealed slightly higher stability. Here, coalescence occurred at centrifugation times higher than 60 min. The pH optimum in terms of emulsion stability was observed at slightly acidic to neutral pH values (pH 6-7).

TABLE 2

Stability of konjac test emulsions at various pH values and centrifugation times t.

| | Emulsion Stability Konjac t/min | | | | |
|---|---|---|---|---|---|
| pH | 1 | 30 | 60 | 120 | 300 |
| 4 | l* | l | l | l | l |
| 5 | m | m | m | l | l |
| 6 | m | m | m | m | m |
| 7 | m | m | m | m | m |
| 8 | m | l | l | l | l |
| 9 | l | l | l | l | l |

*l = low stability: oil and water form two distinct clearly separated phases;
m = medium stability: emulsion partly broken;
h = high stability: no indications of coalescence, optically non-transparent, stable emulsion FIG. 2 shows test emulsions of konjac after centrifugation at 3100 g for t=1 min (a) and t=300 min (b), respectively. The emulsions contained 1.0% (w/w) konjac at different pH values. After centrifugation for t=300 min minor emulsions stabilization was observed at pH 6 and 7, respectively. For all other emulsions extensive coalescence was observed.

Solutions of konjac with concentrations of 0.01%, 0.1%, 0.5%, 1.0%, 1.5%, and 2.0% (w/w) in a simulated intestinal fluid (SIF) without pancreatin according to USP XXII, p. 1789 (pH=7.5, potassium dihydrogenphosphate buffer) were prepared. To 18 g of such a solution 2 g of soya oil (FLUKA, 85471) was added yielding a final oil concentration with respect to the aqueous phase of 10% w/w. Soya oil was not purified and used as received. Emulsions were then prepared using a Miccra homogenization apparatus at 28.000 rpm (level E) and a homogenization time of 1 min. As a reference, mixtures of soya oil and phosphate buffer were used without addition of surfactant. Dying of the emulsion with nile red and subsequent analysis under an optical microscope revealed that the emulsions were of the oil-in-water type. Median droplet size analysis immediately after preparation using a Galai CIS-1 apparatus yielded values of typically 20-30 μm. Glass capillaries of height ca. 95 mm and a diameter of ca. 1.7 mm (glass thickness ca. 0.8 mm) were filled up to ca. 6.5 cm with the pre-prepared emulsions by means of a syringe and centrifuged at a maximum speed of 5000 rpm (Eppendorf, Centrifuge 5403, Rotor No 16A4-44) which corresponds to a centrifugal force of 3100 g (bottom of glass capillary). In order to record the demulsification process, the centrifugation process was interrupted at defined time intervals (t=1, 10, 40, 70, 100, 130, 160, 220, 300 min) and the capillaries placed on an optical scanner operating in transmission mode (Bio-Rad GS-700 Imaging Densitometer). The distance between the capillaries was kept constant by means of a house-made sample holder. All measurements were conducted at room temperature.

Example 2

In Vivo Studies I

To test substances that will ameliorate the oil-related side effects associated with orlistat treatment, an acute human model was developed. Healthy volunteers received orlistat alone or in combination with the test substance during 3 consecutive meals (3-meal test). The modified orlistat formulations used in these 3-meal tests induce 70-80% fat excretion. A questionnaire was given to the volunteers to record side effects. The most severe oil related side effect is oily spotting (uncontrolled loss of oil). This side effect is difficult to quantify accurately in an acute model, however, in some volunteers a spontaneous separation of fat from formed stool was observed. This amount of fat, called free oil (mainly containing triglycerides) was isolated and weighted.

The amount of free oil was used as a surrogate marker for the oily spotting as this is considered necessary for the appearance of oily spotting.

Two clinical studies have been conducted to investigate the gastro-intestinal adverse event modifying effects of numerous substances. It appears that volunteers show an individual sensitivity to the orlistat-related gastro-intestinal side effects. Therefore, each volunteer was used as his own control (treatment with orlistat alone). Volunteers showing a weak sensitivity to orlistat related side effects were excluded from the test evaluation. For a given volunteer a substance is considered as positive when the free oil quantity is reduced by at least 50% compared to the control value (orlistat alone).

Glucomannan was tested as konjac powder. The konjac powder is obtained from the root of a tree (*Amorphophallus konjac*) and this the natural source of glucomannan. This substance was tested in the acute side effect model at the dosage of 4 g/meal. Among the 5 tested volunteers 4 had a decrease by at least 50% of the free oil generated without glucomannan (see table 3). Volunteers treated with glucomannan/orlistat had no fat excretion decrease (compared to volunteers treated with orlistat alone, data not shown) suggesting no interaction of glucomannan with orlistat. No major AEs associated with the glucomannan treatment has been reported.

TABLE 3

| Konjac (Glucomannan) results | | |
| --- | --- | --- |
| Glucomannan | Free oil production (g/week) | |
| (Konjac; 4 g/meal) | orlistat | orlistat + Konjac |
| Test 1 | 11 | 8 |
|  | 9 | 0 |
| Test 2 | 39 | 16 |
|  | 17 | 8 |
|  | 40 | 6 |
| Positive/total (50% < control) |  | 4/5 |

Example 3

In Vivo Studies II

The results from the in vitro experiments were further supported by studies carried out with an in vivo mouse model. The experiment is based on the observation that mice under a high fat diet with orlistat or other lipase inhibitor treatment distribute the excreted free oil over their furs while grooming. Several types and formulations of glucomannan were examined for their ability to reduce or eliminate the production of free oil. The results obtained are shown in FIG. 3.

Example 4

Orlistat Pharmaceutical Compositions

A)

| Ingredient | Quantity mg/Capsule |
| --- | --- |
| orlistat | 120.00 |
| microcrystalline cellulose (AVICEL PH-101) | 93.60 |
| sodium starch glycolate (PRIMOJEL) | 7.20 |
| sodium lauryl sulfate | 7.20 |
| polyvinylpyrrolidone (Povidone K-30) | 12.00 |
| talc | 0.24 |
| Total | 240.24 mg |

Procedure:

1. Blend orlistat, microcrystalline cellulose, and sodium starch glycolate in a suitable mixer.

2. Granulate with a solution of polyvinylpyrrolidone and sodium lauryl sulfate in purified water.

3. Pass the granulation through an extruder and pass the extrudate through a spheronizer to form pellets.

4. Dry the pellets at 30° C.

5. Add talc and mix.

6. Fill into hard gelatin capsules.

B)

| Ingredient | Quantity mg/Capsule |
| --- | --- |
| orlistat | 60 |
| microcrystalline cellulose | 46.8 |
| sodium starch glycolate | 3.6 |
| sodium lauryl sulfate | 3.6 |
| polyvinylpyrrolidone | 6.0 |
| talc | 0.12 |
| Total | 120.12 mg |

Procedure:

1. Blend orlistat, microcrystalline cellulose, and sodium starch glycolate in a suitable mixer.

2. Granulate with solution of polyvinylpyrrolidone and sodium lauryl sulfate in purified water.

3. Pass the granulation through an extruder and pass the extrudate through a spheronizer to form pellets.

4. Dry the pellets at 30° C.

5. Add talc and mix.

6. Fill into hard gelatin capsules.

C)

| Ingredient | Quantity mg/Capsule | |
| --- | --- | --- |
| orlistat | 60 | 120 |
| lactose | 40 | 80 |
| microcrystalline cellulose | 60 | 120 |
| sodium lauryl sulfate | 5.7 | 11.4 |
| sodium starch glycolate | 20 | 40 |
| polyvinylpyrrolidone | 10 | 20 |
| talc | 0.2 | 0.4 |
| Total | 195.9 mg | 391.8 mg |

Procedure:

1. Blend orlistat, lactose, microcrystalline cellulose and sodium starch glycolate in a suitable mixer.

2. Granulate with a solution of polyvinylpyrrolidone and sodium lauryl sulfate in purified water.

3. Pass the granulation through an extruder and pass the extrudate through a spheronizer to form pellets.

4. Dry the pellets at 30° C.

5. Add talc and mix.

6. Fill into hard gelatin capsules.

Example 5

Glucomannan Pharmaceutical Compositions

Composition:

| Ingredient | Quantity g/Chewable tablet |
|---|---|
| glucomannan | 1.5 g |
| sorbitol | 1.1 g |
| lactose anhydrous | 0.376 g |
| talc | 0.16 g |
| sodium stearyl fumarate | 0.064 g |
| Total | 3.2 g |

Procedure:

1. Blend glucomannan, sorbitol and lactose in a suitable mixer.

2. Pass the powder mixture through a sieve.

3. Add talc and sodium stearyl fumarate and mix.

4. Directly compress the powder mixture to a chewable tablet.

Example 6

Glucomannan Pharmaceutical Compositions

Composition:

| Ingredient | Quantity g/Sachet |
|---|---|
| glucomannan | 4 g |
| aspartame | 0.5 g |
| beta-carotene | 0.001 g |
| Total | 4.501 g |

Procedure:

1. Fill glucomannan in a suitable high shear mixer.

2. Granulate with a solution/colloidal suspension of Aspartame and beta-carotene in purified water.

3. Dry the granules at 60° C.

4. Pass the dry granulation through a sieve.

5. Fill into sachets.

Example 7

Glucomannan Pharmaceutical Compositions

Composition:

| Ingredient | Quantity g/Chewable tablet |
|---|---|
| glucomannan | 0.5 g |
| lactose | 0.5 g |
| microcrystalline cellulose | 1.31 g |
| sodium lauryl sulfate | 0.09 g |
| sodium starch glycolate | 0.3 g |
| polivinylpyrrolidone | 0.15 g |
| talc | 0.15 g |
| Total | 3.0 g |

Procedure:

1. Blend glucomannan, lactose, microcrystalline cellulose, sodium starch glycolate in a suitable mixer.

2. Dissolve sodium lauryl sulfate and polivinyl pyrrolidone in purified water.

3. Granulate with the liquid.

4. Pass the granulation through an extruder and pass the extrudate through a spheronizer to form round pellets.

5. Dry the pellets at 65° C.

6. Add talc and mix

7. Compress the pellets to a chewable tablet.

Example 8

Orlistat/Glucomannan Pharmaceutical Compositions

Composition:

| Ingredient | Quantity g/Chewable tablet |
|---|---|
| orlistat | 0.06 g |
| glucomannan | 0.75 g |
| lactose | 0.5 g |
| microcrystalline cellulose | 1.31 g |
| sodium lauryl sulfate | 0.09 g |
| sodium starch glycolate | 0.3 g |
| polivinylpyrrolidone | 0.15 g |
| talc | 0.15 g |
| Total | 3.31 g |

Procedure:

1. Blend orlistat, glucomannan, lactose, microcrystalline cellulose, sodium starch glycolate in a suitable mixer.

2. Dissolve sodium lauryl sulfate and polivinyl pyrrolidone in purified water.

3. Granulate with the liquid.

4. Pass the granulation through an extruder and pass the extrudate through a spheronizer to form round pellets.

5. Dry the pellets at maximum 35° C.

6. Add talc and mix

7. Compress the pellets to a chewable tablet.

Example 9

Orlistat/Glucomannan Pharmaceutical Compositions

Composition:

| Ingredient | Quantity g/Sachet |
|---|---|
| orlistat | 0.12 g |
| glucomannan | 4 g |
| saccharose | 2.8 g |
| beta-carotene | 0.001 g |
| silicium dioxide | 0.5 g |
| Total | 7.421 g |

Procedure:

1. Blend orlistat, glucomannan, sachharose in a suitable mixer.

2. Mix in several portion with the mixture of beta-carotene and silicium dioxide.

3. Fill into sachets.

Example 10

Orlistat/Glucomannan Pharmaceutical Compositions

Composition:

| Ingredient | Quantity g/Chewable tablet |
|---|---|
| orlistat | 0.12 g |
| glucomannan | 2.0 g |
| sodium starch glycolate | 0.1 g |
| microcrystalline cellulose | 0.2 g |
| sodium lauryl sulfate | 0.03 g |
| crospovidone | 0.1 g |
| aspartame | 0.15 g |
| talc | 0.15 g |
| magnesium stearate | 0.03 g |
| Total | 2.85 g |

Procedure:

1. Blend orlistat, glucomannan, microcrystalline cellulose, sodium starch glycolate and crospovidone in a suitable mixer.

2. Granulate with a solution/colloidal suspension of sodium lauryl sulfate and aspartame in purified water.

3. Pass the granulate through a sieve.

4. Dry the granules at 30° C.

5. Pass the dry granules through a sieve.

6. Mix with talc and magnesium stearate.

7. Compress to chewable tablet.

What is claimed:

1. A pharmaceutical composition consisting essentially of from about 0.1% by weight to about 10% by weight, based upon the weight of the composition, of orlistat and from about 20% by weight to about 75% by weight, based upon the weight of the composition, of glucomannan and from about 0.1% to about 80% by weight, based upon the weight of the composition, of one or more pharmaceutically acceptable excipients.

2. The composition of claim 1 wherein the glucomannan is present as konjac.

3. The composition of claim 2 wherein the konjac is present as konjac flour.

4. The composition of claim 2 wherein the konjac contains at least 80% by weight of glucomannan.

5. The pharmaceutical composition of claim 4 wherein the konjac contains at least 90% by weight glucomannan.

6. The composition of claim 1, wherein the pharmaceutically acceptable excipients are selected from the group consisting of fillers, surfactants, disintegrants, binders, lubricants, flowability enhancers, sweeteners, and colorants.

7. The composition of claim 6 wherein the pharmaceutically acceptable excipients are selected from the group consisting of, from about 0.1 to about 20% (w/w) fillers, from about 0.1 to about 10% (w/w) surfactants, from about 0.1 to about 10% (w/w/) disintegrants, from about 0.1 to about 10% (w/w) binder, from about 0.1 to about 10% (w/w) lubricants, from about 0.1 to about 10% (w/w) flowability enhancers, from about 0.1 to about 10% (w/w) sweeteners, from about 0.1 to about 5% (w/w) colorants, and mixtures thereof, with all said weight percents being based upon the weight of the composition.

8. The composition of claim 2 wherein the composition contains from about 5 mg to about 1,000 mg of said orlistat and from about 0.5 g to about 10 g of glucomannan.

9. The composition of claim 8 wherein said composition is in unit oral dosage form.

10. The composition of claim 9 wherein the composition contains from about 0.5 to 6 grams of glucomannan.

11. The composition of claim 10 wherein said composition contains from about 10 mg to 500 mg of orlistat.

12. The composition of claim 11 wherein said composition contains from about 10 mg to about 360 mg of orlistat.

13. The composition of claim 8, wherein the pharmaceutically acceptable excipients are selected from the group consisting of fillers, surfactants, disintegrants, binders, lubricants, flowability enhancers, sweeteners, and colorants.

14. The composition of claim 13, wherein the pharmaceutically acceptable excipients are selected from the group consisting of from about 0.1 to about 10 g fillers, from about 0.05 to about 5.0 g surfactants, from about 0.001 to about 1.0 g lubricants, from about 0.1 to about 5.0 g flowability enhancers, from about 0.01 to about 4.0 g sweeteners, from about 0.001 to about 0.5 g colorants, and mixtures thereof.

15. A pharmaceutical composition consisting of from about 0.1% by weight to about 10% by weight, based upon the weight of the composition, of orlistat and from about 20% by weight to about 75% by weight, based upon the weight of the composition, of glucomannan and from about 0.1% to about 80% by weight, based upon the weight of the composition, of one or more pharmaceutically acceptable excipients.

16. The composition of claim 15 wherein the glucomannan is present as konjac.

17. The composition of claim 16 wherein the konjac is present as konjac flour.

18. The composition of claim 16 wherein the konjac contains at least 80% by weight of glucomannan.

19. The pharmaceutical composition of claim 18 wherein the konjac contains at least 90% by weight glucomannan.

20. The composition of claim 15, wherein the pharmaceutically acceptable excipients are selected from the group consisting of fillers, surfactants, disintegrants, binders, lubricants, flowability enhancers, sweeteners, and colorants.

21. The composition of claim 20 wherein the pharmaceutically acceptable excipients are selected from the group consisting of, from about 0.1 to about 20% (w/w) fillers, from about 0.1 to about 10% (w/w) surfactants, from about 0.1 to about 10% (w/w/) disintegrants, from about 0.1 to about 10% (w/w) binder, from about 0.1 to about 10% (w/w) lubricants, from about 0.1 to about 10% (w/w) flowability enhancers, from about 0.1 to about 10% (w/w) sweeteners, from about 0.1 to about 5% (w/w) colorants, and mixtures thereof, with all said weight percents being based upon the weight of the composition.

22. The composition of claim 16 wherein the composition contains from about 5 mg to about 1,000 mg of said orlistat and from about 0.5 g to about 10 g of glucomannan.

23. The composition of claim 22 wherein said composition is in unit oral dosage form.

24. The composition of claim 23 wherein the composition contains from about 0.5 to 6 grams of glucomannan.

25. The composition of claim 24 wherein said composition contains from about 10 mg to 500 mg of orlistat.

26. The composition of claim 25 wherein said composition contains from about 10 mg to about 360 mg of orlistat.

27. The composition of claim 22, wherein the pharmaceutically acceptable excipients are selected from the group consisting of fillers, surfactants, disintegrants, binders, lubricants, flowability enhancers, sweeteners, and colorants.

28. The composition of claim 27, wherein the pharmaceutically acceptable excipients are selected from the group consisting of from about 0.1 to about 10 g fillers, from about 0.05 to about 5.0 g surfactants, from about 0.001 to about 1.0 g lubricants, from about 0.1 to about 5.0 g flowability enhancers, from about 0.01 to about 4.0 g sweeteners, from about 0.001 to about 0.5 g colorants, and mixtures thereof.

29. A pharmaceutical composition comprising from about 0.1% by weight to about 10% by weight, based upon the weight of the composition, of orlistat and from about 20% by weight to about 75% by weight, based upon the weight of the composition, of glucomannan and from about 0.1% to about 80% by weight, based upon the weight of the composition, of one or more pharmaceutically acceptable excipients.

30. The composition of claim 29 wherein the glucomannan is present as konjac.

31. The composition of claim 30 wherein the konjac is present as konjac flour.

32. The composition of claim 30 wherein the konjac contains at least 80% by weight of glucomannan.

33. The pharmaceutical composition of claim 32 wherein the konjac contains at least 90% by weight glucomannan.

34. The composition of claim 29, wherein the pharmaceutically acceptable excipients are selected from the group consisting of fillers, surfactants, disintegrants, binders, lubricants, flowability enhancers, sweeteners, and colorants.

35. The composition of claim 34 wherein the pharmaceutically acceptable excipients are selected from the group consisting of, from about 0.1 to about 20% (w/w) fillers, from about 0.1 to about 10% (w/w) surfactants, from about 0.1 to about 10% (w/w/) disintegrants, from about 0.1 to about 10% (w/w) binder, from about 0.1 to about 10% (w/w) lubricants, from about 0.1 to about 10% (w/w) flowability enhancers, from about 0.1 to about 10% (w/w) sweeteners, from about 0.1 to about 5% (w/w) colorants, and mixtures thereof, with all said weight percents being based upon the weight of the composition.

36. The composition of claim 30 wherein the composition contains from about 5 mg to about 1,000 mg of said orlistat and from about 0.5 g to about 10 g of glucomannan.

37. The composition of claim 36 wherein said composition is in unit oral dosage form.

38. The composition of claim 37 wherein the composition contains from about 0.5 to 6 grams of glucomannan.

39. The composition of claim 38 wherein said composition contains from about 10 mg to 500 mg of orlistat.

40. The composition of claim 39 wherein said composition contains from about 10 mg to about 360 mg of orlistat.

41. The composition of claim 36, wherein the pharmaceutically acceptable excipients are selected from the group consisting of fillers, surfactants, disintegrants, binders, lubricants, flowability enhancers, sweeteners, and colorants.

42. The composition of claim 41, wherein the pharmaceutically acceptable excipients are selected from the group consisting of from about 0.1 to about 10 g fillers, from about 0.05 to about 5.0 g surfactants, from about 0.001 to about 1.0 g lubricants, from about 0.1 to about 5.0 g flowability enhancers, from about 0.01 to about 4.0 g sweeteners, from about 0.001 to about 0.5 g colorants, and mixtures thereof.

* * * * *